United States Patent
Spagnoli et al.

(10) Patent No.: US 9,539,068 B2
(45) Date of Patent: Jan. 10, 2017

(54) IMPLANTABLE SCREW AND SYSTEM FOR SOCKET PRESERVATION

(75) Inventors: Daniel B. Spagnoli, Charlotte, NC (US); Todd A. Mobley, Collierville, TN (US); Jeffrey L. Scifert, Arlington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 438 days.

(21) Appl. No.: 12/508,616

(22) Filed: Jul. 24, 2009

(65) Prior Publication Data

US 2011/0020768 A1    Jan. 27, 2011

(51) Int. Cl.
*A61C 8/00*    (2006.01)

(52) U.S. Cl.
CPC ............ *A61C 8/008* (2013.01); *A61C 8/0024* (2013.01); *A61C 8/0075* (2013.01); *A61C 2008/0084* (2013.01)

(58) Field of Classification Search
CPC .......................................... A61C 8/00–8/0098
USPC .................................................. 433/172–176
See application file for complete search history.

(56) References Cited

U.S. PATENT DOCUMENTS

| | | | |
|---|---|---|---|
| 3,579,831 A | 5/1971 | Stevens et al. | |
| 3,797,113 A * | 3/1974 | Brainin ................ | A61C 8/0018 433/173 |
| 5,145,372 A * | 9/1992 | Daftary ................. | A61C 8/005 433/173 |
| 5,176,680 A | 1/1993 | Vignaud et al. | |
| 5,201,733 A | 4/1993 | Etheredge, III | |
| 5,599,185 A * | 2/1997 | Greenberg ............. | A61C 8/008 433/173 |
| 5,755,575 A | 5/1998 | Biggs | |
| 5,839,899 A | 11/1998 | Robinson | |
| 5,899,940 A | 5/1999 | Carchidi et al. | |
| 5,971,985 A | 10/1999 | Carchidi et al. | |
| 5,972,368 A | 10/1999 | McKay | |
| 6,120,292 A | 9/2000 | Buser et al. | |
| 6,146,420 A | 11/2000 | McKay | |
| 6,238,214 B1 | 5/2001 | Robinson | |
| 6,290,500 B1 | 9/2001 | Morgan et al. | |
| 6,325,627 B1 | 12/2001 | Ashman | |
| 6,394,807 B2 | 5/2002 | Robinson | |
| 6,402,518 B1 | 6/2002 | Ashman | |

(Continued)

FOREIGN PATENT DOCUMENTS

| | | |
|---|---|---|
| DE | 4329788 B4 | 5/2007 |
| EP | 1688103 A1 | 8/2006 |

OTHER PUBLICATIONS

Ace Bone Grafting and Ridge Split Augmentation Catalog, 2004; see p. 4.

(Continued)

*Primary Examiner* — Matthew Nelson
(74) *Attorney, Agent, or Firm* — Sorell Lenna & Schmidt LLP

(57) ABSTRACT

An implantable screw for preserving the integrity of an oral socket and for maintaining space during bone grafting procedures is provided, where the screw has a healing abutment head having a region adapted to support soft tissue, a threaded shaft and a tip adapted to penetrate bone tissue. The temporary implantable screws provided may be used in conjunction with bone graft materials and are removable for placement of an oral implant.

19 Claims, 2 Drawing Sheets

(56) References Cited

U.S. PATENT DOCUMENTS

| | | | |
|---|---|---|---|
| 6,716,030 B1* | 4/2004 | Bulard | A61C 8/0048 433/174 |
| 6,722,884 B2* | 4/2004 | Ashman | A61C 8/0036 433/173 |
| 6,761,738 B1 | 7/2004 | Boyd | |
| 6,949,100 B1 | 9/2005 | Venturini | |
| 7,074,426 B2 | 7/2006 | Kochinke | |
| 7,090,493 B2 | 8/2006 | Chang | |
| 7,166,570 B2 | 1/2007 | Hunter et al. | |
| 7,309,232 B2 | 12/2007 | Rutherford et al. | |
| 7,322,978 B2 | 1/2008 | West, Jr. | |
| 2005/0019730 A1* | 1/2005 | Gittleman | A61C 8/0022 433/174 |
| 2005/0079469 A1* | 4/2005 | Akagawa | A61C 8/0012 433/173 |
| 2006/0110707 A1* | 5/2006 | Perez Davidi | A61C 8/0022 433/173 |
| 2006/0292524 A1* | 12/2006 | Lorenzon | A61C 8/0018 433/174 |
| 2007/0099152 A1* | 5/2007 | Busch | A61C 8/0001 433/173 |
| 2007/0190490 A1* | 8/2007 | Giorno | A61C 8/0022 433/173 |
| 2008/0004623 A1 | 1/2008 | Ferrante et al. | |
| 2008/0020349 A1* | 1/2008 | Dricot | A61C 8/0012 433/174 |
| 2008/0095709 A1 | 4/2008 | Ella | |
| 2009/0061388 A1* | 3/2009 | Collins | A61C 8/0006 433/174 |
| 2009/0075235 A1* | 3/2009 | Letcher | A61C 8/0048 433/173 |
| 2009/0191508 A1* | 7/2009 | Choi | A61C 8/005 433/174 |
| 2010/0003638 A1* | 1/2010 | Collins | A61C 8/0012 433/174 |
| 2010/0055645 A1* | 3/2010 | Mullaly | A61C 8/0025 433/174 |

OTHER PUBLICATIONS

Kao, et al.; Tissue Engineering for Periodontal Regeneration; CDA Journal, vol. 33, No. 3, pp. 205—Mar. 2005.
Rose; Bone Grafts and Growth and Differentiation Factors for Regenerative Therapy: A Review; Prac. Proc. Aesthet. Dent. 2001; 13(9):725-734.
U.S. Appl. No. 12/179,471, filed Jul. 24, 2008.
U.S. Appl. No. 12/392,163, filed Feb. 25, 2009.

* cited by examiner

IMPLANTABLE SCREW AND SYSTEM FOR SOCKET PRESERVATION

BACKGROUND

The successful use of dental implants has long been known and is well documented in the field. Despite successful dental implant procedures through the years, the success of the placement of a dental implant is limited by the quality and quantity of existing bone of a given patient. Due to the destructive nature of dentures to the underlying jawbone the amount of bone in many people is very limited for the placement of dental implants.

Furthermore, atrophy of the jawbone can occur when the bone is not subjected to occlusal loads. Therefore, atrophy may occur over time when a tooth is not replaced with a dental implant. As a result, when a person has been partially endentulous for a long period of time, they may suffer from an atrophic alveolar ridge that is not capable of securely supporting a dental implant. The deterioration of the alveolar ridge has severe consequences, including reducing one's ability to masticate and compromising aesthetics.

Immediate dental implant placement is ideal, but is not always an option for many patients. Preservation of the alveolar ridge is key to preventing a collapse of the alveolar bone and soft tissue, preventing a collapse of the alveolar ridge causing irregularities in alveolar form, and maintaining an oral socket after extraction for later placement of an implant. Thus, preserving existing bone minimizes the potential obstacles to implant placement created by atrophic jawbone.

Additionally, grafting bone is also a means to ensure that adequate bone is present for supporting dental implants. There are many known methods of bone grafting. Bone grafting procedures may incorporate bone graft material in order to stimulate bone growth. As viable exemplary methods, blocks of hip bone have been affixed to the jaw and freeze-dried demineralized bone protein has been used as a stimulant to cause the patient's bone cells to become active and lay down new bone onto the existing bone areas and into the new bone graft areas. Through experience and research, it has become evident that, for bone grafting to be successful, it must be given an isolated space to grow, protected from muscular pressure, tissue impingement and forces of mastication. In order to create this space, fabric-like membranes or barriers have been used over a bony defect. Although this barrier creates an isolated space from the invasion of connective tissue cells into the bony defect or bone graft area, it does not create a protected space from chewing forces or tissue pressure. It is necessary to protect the growing bone from all aspects of potential harm. Therefore, in many instances the space is created and maintained utilizing dental implants and supports including a tenting-type support screw.

SUMMARY

A new implantable screw is provided for preserving the integrity of an endentulous oral socket. This screw comprises a healing abutment head, a threaded shaft and a tip adapted to penetrate bone. The healing abutment head may be 3, 4 or 5 mm in height and may have a a straight wall design, where the diameter of the head is consistent and ranges from about 3 mm to about 6 mm. The threaded shaft is used to anchor the screw in the existing jawbone and may vary in size. The shaft may have an outer diameter of 2.0 mm or less and an inner diameter of 1.8 mm or less, where the inner diameter is less than the outer diameter. This screw may be used with bone growth materials and is removable for placement of a dental implant.

In another embodiment of the implantable screw for preserving the integrity of an oral socket, the screw comprises a healing abutment head, a threaded shaft and a tip adapted to penetrate bone. The healing abutment head may be 3, 4 or 5 mm in height and may have a flared design where the diameter of the head at the bottom base is less than the diameter of the head at the top surface. In the flared head design, the diameter ranges from about 3 mm to about 6 mm at the bottom base and increases by 1, 1.5 or 2 mm at the top surface. The threaded shaft is used to anchor the screw in the existing jawbone and may vary in size. The shaft may have an outer diameter of 2.0 mm or less and an inner diameter of 1.8 mm or less, where the inner diameter is less than the outer diameter. This screw may be used with bone growth materials and is removable for placement of a dental implant.

Additionally, a method of using an implantable screw device for preserving the integrity of an endentulous oral socket is provided. The method comprises implanting a device comprising at least one implantable screw into the jawbone. The implantable screw comprises a healing abutment head, a threaded shaft, and a tip. The head may range in size, but typically is between about 3 mm to about 5 mm in height and between about 3 mm to about 6 mm in diameter at the bottom base of the head. The shaft of the screw is threaded for anchoring the screw in the bone and has an outer diameter of 2.0 mm or less and an inner diameter of the shaft is 1.8 mm or less, where the inner diameter is less than the outer diameter. The tip of the screw is adapted to penetrate bone tissue. The method further comprises incorporating a bone growth material around the device to stimulate bone growth and removing the device in order to affix an oral implant.

Additional features and advantages of various embodiments will be set forth in part in the description that follows, and in part will be apparent from the description or figures, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
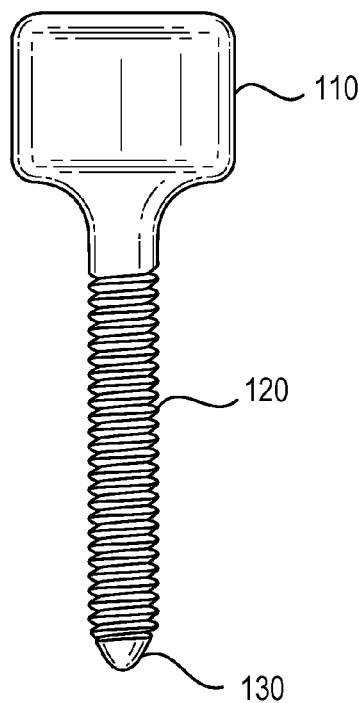
FIG. 1: illustrates an implantable screw including a healing abutment head having a straight wall design, a threaded shaft and a tip adapted to penetrate bone tissue.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "an implantable screw" includes one, two, three or more implantable screws.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

Provided herein is an implantable screw for preserving the integrity of an oral socket and for maintaining space during bone grafting procedures in a patient in need of such treatment. As an illustrative example, not a limitation, the screw can be implanted immediately or shortly after the extraction of a tooth and can be used in oral and maxillofacial surgical procedures for alveolar ridge preservation and/or augmentation as well as other surgical procedures such as the treatment of orofacial diseases.

The screw can be implanted into orofacial tissue, which includes tissue sites located within the oral cavity. Such tissue includes by way of illustration and not limitation, periodontal tissue such as the periodontium; periodontal ligaments; bone tissue at the end of an infected tooth, inside the tooth or within the bone cavity such as may be present after an apicoectomy or tooth extraction; endodontic tissue; bone tissue surrounding an implant fixture; jaw tissue such as the temporomandibular joint, the temporalis muscle, the temporal bone the masseter muscle and the mandible; tissue affected by surgery, e.g. tonsillectomy; and so forth.

The screw can be used to treat different orofacial diseases. The term "orofacial disease" is intended to encompass diseases within the orofacial environment, as well as diseases that originate in the orofacial environment. The term "orofacial disease" is intended to include, by way of illustration and not limitation, acute and chronic inflammation, including chronic inflammation of the tissue (including host response reactions) to stop the process of the on-going tissue decay; infection; pain and related inflammatory and other complications of mechanical teeth cleaning (including root planning and scaling), all periodontal surgical procedures, and other surgical procedures such as an apicoectomy or root canal, procedures done to facilitate tooth movement such as orthodontia; repair damage to periodontal ligament, bone and other tissues that has been caused by periodontal disease; cranomandibular disease which produces facial, head, ear and jaw pain, examples of which include temporomandibular joint syndrome; cosmetic and plastic surgery to reconstruct and rebuild facial features after accidents or other deformations or the like.

Treating or treatment of a disease refers to executing a protocol, which may include implanting one or more implantable screws into a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

In some embodiments, the implantable screw disclosed herein allows surgeons to preserve existing bone and to prevent the degradation of the alveolar ridge due to the loss of compressive forces. Further, various embodiments allow surgeons to utilize existing bone graft materials to treat bony defects in which space maintenance is crucial for success, but in which limited options for maintaining that space currently exist. The screw can be used for socket preservation, space maintenance or alveolar ridge augmentation, where increase in volume and bone is desired. An alveolar ridge (also known as the alveolar process) comprises the portion of bone in the upper jaw (the maxilla) or the lower jaw (the mandible) that surrounds and supports the teeth. The implantable screw preserves the existing bone of the alveolar ridge and when these areas do not contain enough native bone for dental implant placement or stabilization, and the volume of bone needs to be increased the screw supports the growth of the new bone.

In various embodiments, the implantable screw provides space between the bone and gingival. Gingival tissue includes part of the soft tissue lining of the mouth. It surrounds the teeth and provides a seal around them. Compared with the soft tissue linings of the lips and cheeks, most of the gingiva are tightly bound to the underlying bone and are designed to resist the friction of food passing over them. Thus the implantable screw supports the gingival tissue so that bone can regenerate and restore the proper jaw structure for proper aesthetics and for dental implant-borne restoration.

The implantable screw is designed to have a larger head and a smaller shaft as compared to other screws used for socket preservation. The head is designed as a healing abutment with smooth rounded edges to provide an interface that will not be harmful to the gingival or mucosal tissue. Further, the under surface of the head of the screw maintains space between the bone and the gingival. The space between the bone and gingival tissue provide room for bone growth, adequate for restoration of proper jaw structure, for proper aesthetics and for dental implant-borne restorations. In some instances, the space is used to support bone graft material to further encourage bone growth. Thus, the implantable screw provides an attractive option to surgeons seeking socket preservation and space maintenance materials to use with bone grafting and bone regenerative products.

The figures and corresponding descriptions below are not meant to limit the disclosure in any way; embodiments illustrated and described in connection with any one figure may be used in conjunction with embodiments illustrated and described in connection with any other figure unless otherwise expressly provided.

FIGS. 1-5 illustrate various embodiments of socket preservation screws for use as implantable devices generally referred to by the reference numerals 110-580, respectively. Similar reference numbers will be used throughout the drawings to refer to similar portions of similar parts.

FIG. 1 illustrates an implantable screw for temporarily preserving the integrity of an oral socket after extraction. The implantable screw can be used to maintain or create space during bone grafting in certain dental regenerative procedures. In various embodiments the implantable screw comprises a healing abutment head having a straight wall design 110, a threaded shaft 120, and a tip 130 adapted to penetrate bone tissue.

The head of the screw has smooth, contoured edges to support the interface between the gingival tissue and the screw head, minimizing the likelihood of dehiscence or piercing of the soft tissue in the jaw region. Further, the surface of the healing abutment head is polished using known methods such as buffing so that the finished surface is smooth and grainless. A polished surface allows the screw to be resistant to plaque and tarter build-up. Machining operations such as Computer Numerical Control (CNC) or lathe are also used to manufacture the surface and geometry of the screws during production.

The head may be provided in various sizes. The height of the head will be about 3 mm to about 5 mm to simulate the normal soft tissue sulcus depth of about 3 mm. A taller screw may be used if needed to accommodate for variations in crestal bone height. Typically the head will range in diameter size between about 3 mm and about 6 mm, providing 1 mm incremental increases. Typical head sizes are 3 mm, 4 mm, 5 mm or 6 mm. In the straight wall design, the diameter of the healing abutment is consistent from the top surface of the head to the bottom base of the head.

The shaft of the implantable screw allows the user (e.g., surgeon, dentist or other health care provider) to anchor the screw in the bone. In some embodiments the shaft of the implantable screw is fully threaded, i.e., from tip to head. The threading pitch of the shaft is such that primary stability of the screw may be attained after engagement of about 3 mm to about 4 mm of bone.

The screw shaft has a smaller than normal diameter to preserve existing bone as well as to increase the available space for bone growth. Further, the small shaft helps to minimize the impact on new host bone upon removal of the screw. Various embodiments provide a shaft having an outer diameter of about 2.0 mm or less and an inner diameter of about 1.8 mm or less. Typically, the inner diameter will be less than the outer diameter. Typically, the outer diameter will be about 1.4 mm and the inner diameter will be about 1.2 mm.

The length of the shaft is also variable depending on the requirements. The shaft length may range between about 8 mm and about 17 mm, providing 1 mm incremental increases. Typical lengths provided in various embodiments include, 8 mm, 9 mm, 10 mm, 11 mm, 12 mm, 13 mm, 14 mm, 15 mm, 16 mm, or 17 mm.

The tip of the implantable screw is adapted to penetrate bone tissue. The tip may be of any shape that is commonly used for such purpose. The screw may be either self-drilling or may be adapted for self-tapping and self-drilling after minimal pilot.

In some embodiments, the screw can be a single component and in other embodiments, the screw can comprise a separate head, shaft and tip that connect together. In some embodiments, the screw may be positioned solely for socket preservation or may be used in a variety of procedures including those procedures requiring vertical or lateral augmentation of the alveolar ridge.

The implantable screw is typically used as a temporary means to preserve an oral socket. For placement of a dental implant or once a desired amount of new host bone has been generated, the implantable screw is removable. In some embodiments, the screw is implanted for a period of time of less than one year. Typical temporary periods include, one day to two weeks, one day to three weeks, one day to one month, one day to two months, one day to three months, one day to four months, one day to five months, one day to six months, one day to seven months, one day to eight months, one day to nine months, one day to ten months, one day to eleven months, and one day to one year.

The dimensions of the head and shaft are such that the oral cavity is preserved and the impact and potential damage to the bone upon removal is minimized. The removal of the socket preservation screw provides a region of bone ideally sufficient to support the placement of an oral implant. The amount of desired host bone is dependent on the specific purpose of the procedure. In some embodiments the implant may be inserted into the same space left vacant by the removal of the implantable screw.

Figure 2:
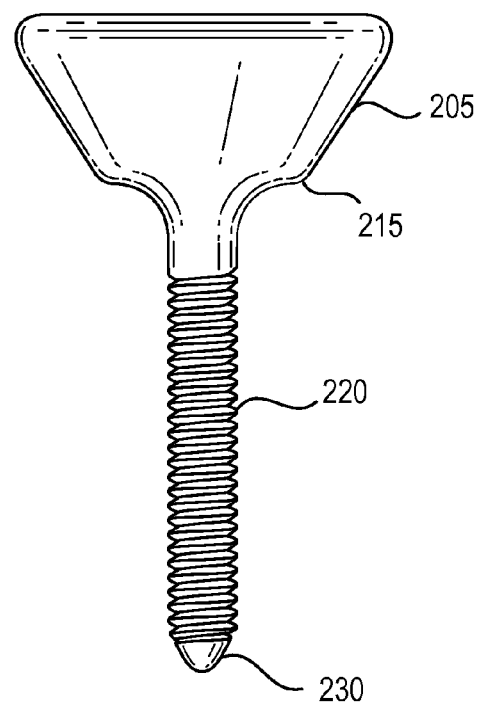
FIG. 2: illustrates an implantable screw including a healing abutment head having a flared design, a threaded shaft and a tip adapted to penetrate bone tissue.

FIG. 2 illustrates another embodiment of an implantable screw for temporarily preserving the integrity of an oral socket after extraction. The implantable screw can be used to maintain or create space during bone grafting in certain dental regenerative procedures. The implantable screw comprises a healing abutment head having a flared design 210, a threaded shaft 220, and a tip 230 adapted to penetrate bone tissue.

The head of the screw has smooth, contoured edges to support the interface between the gingival tissue and the screw head, minimizing the likelihood of dehiscence or piercing of the soft tissue in the jaw region. Further, the surface of the screw is also smooth, grainless and polished to resist plaque and tarter build-up.

Similarly to the straight wall design, the head of the flared design may be provided in various sizes. The height of the head will be about 3 mm to about 5 mm to simulate the normal soft tissue sulcus depth of about 3 mm and a taller screw may be used if needed to accommodate for variations in crestal bone height. Typically the head will range in diameter size between about 3 mm and about 6 mm, providing 1 mm incremental increases. Typical head sizes are 3 mm, 4 mm, 5 mm or 6 mm. In a flared design, the diameter of the head may increase at the top surface of the head 205 relative to the bottom base of the head 215. In the flared design, the top surface of the head may be 1, 1.5 or 2 mm larger than the diameter at the bottom base of the head.

In some embodiments the shaft of the implantable screw is fully threaded, i.e., from tip to head. The threading pitch of the shaft is such that primary stability of the screw may be attained after engagement of about 3 mm to about 4 mm of bone. Typically, the shaft has an outer diameter of about 2.0 mm or less and an inner diameter of about 1.8 mm or less, where the inner diameter is less than the outer diameter. Typically, the outer diameter will be about 1.4 mm and the inner diameter will be about 1.2 mm.

The length of the shaft is also variable depending on the requirements. The shaft length may range between about 8 mm and about 17 mm, providing 1 mm incremental increases. Typical lengths provided in various embodiments include, 8 mm, 9 mm, 10 mm, 11 mm, 12 mm, 13 mm, 14 mm, 15 mm, 16 mm, or 17 mm.

The tip of the implantable screw is adapted to penetrate bone tissue. The tip may be of any shape that is commonly used for such purpose. The screw may be either self-drilling or may be adapted for self-tapping and self-drilling after minimal pilot.

The implantable screw is typically used as a temporary means to preserve an oral socket. For placement of a dental implant or once a desired amount of new host bone has been generated, the implantable screw is removable. In some embodiments, the screw is implanted for a period of time of less than one year. Typical temporary periods include, one day to two weeks, one day to three weeks, one day to one month, one day to two months, one day to three months, one day to four months, one day to five months, one day to six months, one day to seven months, one day to eight months, one day to nine months, one day to ten months, one day to eleven months, and one day to one year.

The dimensions of the head and shaft are such that the oral cavity is preserved and the impact and potential damage to the bone upon removal is minimized. The removal of the socket preservation screw provides a region of bone ideally sufficient to support the placement of an oral implant. The amount of desired host bone is dependent on the specific purpose of the procedure. In some embodiments the implant may be inserted into the same space left vacant by the removal of the implantable screw.

Figure 3:
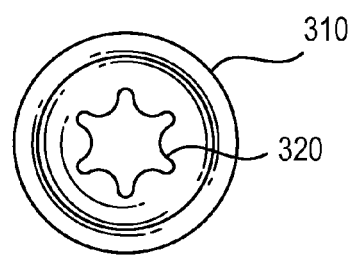
FIG. 3: illustrates the top view of the healing abutment head of an implantable screw.

FIG. 3 illustrates an exemplary top view of the healing abutment head 310 of an implantable screw. In various embodiments, the head of the screw may have one or more recesses and/or projections 320 that may be any size and shape e.g., straight, flat-sided shape, an elliptical shape, bi-concave shape, square shape, or any other protruding or recessed shape which provides sufficient implantation tool-engaging end strength and drive purchase to allow transmission of insertional torque without breaking or otherwise damaging the implantable screw. Typically a screw can be turned by hand, drill or other dental instrument designed to turn the screw clockwise or counterclockwise as needed so that the tip can penetrate the bone.

Implantation tools include, but are not limited to a driver, wrench, spanner, screwdriver, or other turning tool, and the like that can engage the implantable device. The implantation tool may be used manually (e.g., turnable by hand) or by an automatic device (e.g., using a drill, power driver, etc.). Exemplary embodiments may employ the use of a torx or star drill.

Figure 4:
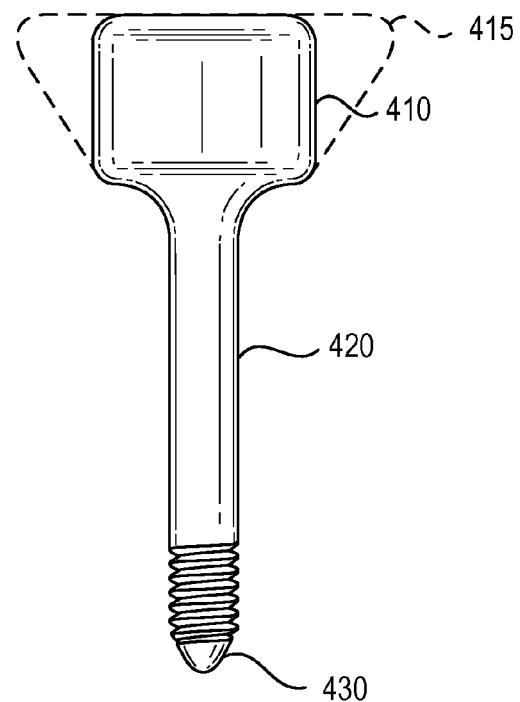
FIG. 4: illustrates an implantable screw including a healing abutment head, a partially threaded shaft and a tip adapted to penetrate bone tissue.

In another exemplary embodiment, FIG. 4 illustrates an implantable screw as previously described, having a healing abutment head, with smooth, contoured edges and a curved under surface. The healing abutment head may either comprise a straight wall design 410 or a flared design 415. The implantable screw further comprises a shaft 420 and tip 430. In some embodiments the shaft of the screw is threaded on the apical or coronal regions of the screw so the entire length of the shaft is threaded or less than the entire length of the shaft is threaded. Typically the threading initiates at the tip of the screw and proceeds up toward the head providing at least enough threading to ensure stabilization of the screw. In various embodiments, the thread pitch is sufficient to stabilize the screw after engaging about 3 mm to about 4 mm of bone.

Figure 5:
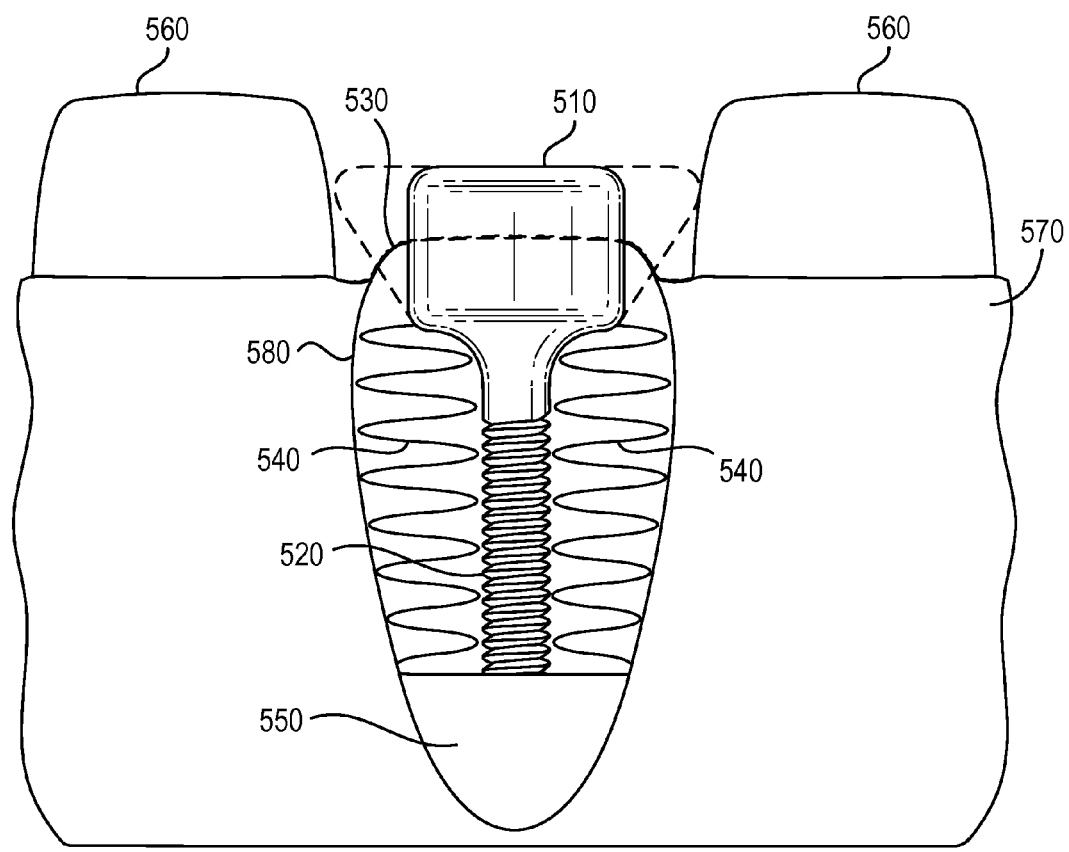
FIG. 5: illustrates a cross-sectional view of an implantable screw, implanted in the jawbone of a patient where the healing abutment screw head is visible amidst existing teeth and/or implants in the mouth of the patient.

FIG. 5 illustrates the jawline of a patient with a cross-section view of the oral socket 580. The head of the implantable screw 510 emerges from the closure of the oral socket and sits proud above the gumline 570. Thus, the head of the screw is visible as it sits between existing teeth and/or dental implants 560.

Typically, the screw head is in the shape of a healing abutment where the healing abutment is either a straight wall or flared design. The screw head may vary in diameter size. Typically a screw head may have a diameter of either 3 mm, 4 mm, 5 mm or 6 mm. The size may vary depending on the available space and what the procedure necessitates. In a flared design, the diameter of the head may increase at the top surface of the head by 1, 1.5 or 2 mm as compared to the diameter at the bottom base of the head.

The shaft of the implantable screw 520 may be either fully or partially threaded such that the screw may be anchored into the jawbone 550. In the exemplary embodiment, stability of the screw will be attained after about 3 mm to about 4 mm of engagement with the jawbone.

The shaft of the implantable screw may also range in diameter and length. The diameter of the shaft is small in order to leave more room for new bone as well as to minimize the amount of bone impacted upon removal. Some embodiments provide that the outer diameter of each implantable screw is about 2.0 mm or less while the inner diameter is about 1.8 mm or less. Typically, the inner diameter is less than the outer diameter. Further the length of the shaft may vary in the range of about 8 mm to about 17 mm.

In some embodiments, bone growth material 540 is incorporated to encourage the development of new bone. Bone growth materials for stimulating bone growth may be artificial, synthetic, natural, or natural substitutes. Bone growth materials may be provided to the socket in a variety of ways, including by way of example, coating the screw with the bone growth material or injection of a bone growth agent into the socket. The type of growth agent and the quantity needed will depend on the patient and the type of procedure required.

In the case where a soft tissue closure is required to protect a graft, the surgeon makes a combination of vertical releasing incisions extending from the mesial and distal of the facial aspect of the socket and then completes a horizontal periosteal releasing incision to advance the flap. Although this procedure permits closure of the tissue edges it leads to distortion of important gingival and papilla relationships. In various embodiments, the soft tissue 530 is sutured in direct apposition to the circumference of the screw head, eliminating the need to use flaps or barrier membranes to protect the graft, and also preserving the anatomy of the gingival and papilla tissue.

In some embodiments, the jawbone is prepared using conventional surgical procedures and the device can be inserted in accordance with the conventional means.

The specific dimensions of each screw described herein may vary depending on the requirements of the particular application or the necessitated procedure.

Therapeutic Agents

Various embodiments of the implantable screw can be mixed, sprayed and/or coated with one or more therapeutic agents to provide an effective amount of the therapeutic agent. Alternatively, the therapeutic can be coated or impregnated on a carrier. In that case, the screw may be passed through the carrier or the carrier may be packed around the screw.

Therapeutic agents include, but are not limited to, analgesics, anti-inflammatory agents, anti-infective agents, antibiotics, bisphosphonates or other anti-resorptive agents (e.g., calcitonin), and/or growth factors. Bisphosphonates include, but are not limited to, pamidronate, alendronate, zolendronate, 3-(N,N-dimethylamino)-1-hydroxypropane-1,1-diphosphonic acid, e.g. dimethyl-APD; 1-hydroxy-ethylidene-1,1-bisphosphonic acid, e.g. etidronate; 1-hydroxy-3 (methylpentylamino)-propylidene-bisphosphonic acid, (ibandronic acid), e.g. ibandronate; 6-amino-1-hydroxyhexane-1,1-diphosphonic acid, e.g. amino-hexyl-BP; 3-(N-methyl-N-pentylamino)-1-hydroxypropane-1,1-diphosphonic acid, e.g. methyl-pentyl-APD; 1-hydroxy-2-(imidazol-1-yl)ethane-1,1-diphosphonic acid, e.g. zoledronic acid; 1-hydroxy-2-(3-pyridyl)ethane-1,1-diphosphonic acid (risedronic acid), e.g. risedronate; 3-[N-(2-phenylthioethyl)-N-methylamino]-1-hydroxypropane-1,1-bishosphonic acid; 1-hydroxy-3-(pyrrolidin-1-yl)propane-1,1-bisphosphonic acid, 1-(N-phenylaminothiocarbonyl)methane-1,1-diphosphonic acid, e.g. FR 78844 (Fujisawa); 5-benzoyl-3,4-dihydro-2H-pyrazole-3,3-diphosphonic acid tetraethyl ester, e.g. U81581 (Upjohn); or 1-hydroxy-2-(imidazo[1,2-a]pyridin-3-yl)ethane-1,1-diphosphonic acid, e.g. YM 529, or combinations thereof or the like.

An effective amount of the therapeutic agent is such that when administered, the drug results in alteration of the biological activity, such as, for example, inhibition of inflammation, reduction or alleviation of pain, growth of bone, etc.

A therapeutic agent can be an analgesic. "Analgesic" refers to an agent or compound that can reduce, relieve or eliminate pain. Examples of analgesic agents include but are not limited to acetaminophen, a local anesthetic, such as for example, lidocaine, bupivicaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The phrase "anti-inflammatory agent" refers to an agent or compound that has anti-inflammatory effects. These agents may remedy pain by reducing inflammation. Examples of anti-inflammatory agents include, but are not limited to, a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketorolac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

In various embodiments, the therapeutic agent can comprise BMPs and/or CDMPs including, but not limited to, BMP-2, BMP-4, BMP-6, BMP-7, BMP-8, and CDMP-1.

Anti-infective agents to treat infection include by way of example and not limitation, antibacterial agents; quinolones and in particular fluoroquinolones (e.g., norfloxacin, ciprofloxacin, lomefloxacin, ofloxacin, etc.), aminoglycosides (e.g. gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Other exemplary antibacterial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natamycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

In various embodiments, the implantable screw comprises material, such as for example, polyurethane, polyurea, polyether(amide), PEBA, thermoplastic elastomeric olefin, copolyester, and styrenic thermoplastic elastomer, steel, aluminum, stainless steel, titanium, zirconium, carbon, metal alloys with high non-ferrous metal content and a low relative proportion of iron, carbon fiber, glass fiber, plastics, ceramics or combinations thereof.

In various embodiments, the screw comprises biopolymers including but not limited to poly(alpha-hydroxy acids), poly(lactide-co-glycolide) (PLGA), polylactide (PLA), polyglycolide (PG), polyetheretherketone (PEEK), polyethylene glycol (PEG) conjugates of poly(alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

In other embodiments the screw comprises "resorbable" materials of either synthetic or natural origin. Such materials are degraded through enzymatic, hydrolytic or other chemical reactions or cellular processes into by-products that are either integrated into, or expelled from, the body. Resorbable materials include, but are not limited to cortical bone, ceramic (e.g., hydroxyapatite, tricalcium phosphate, bioglasses, calcium sulfate, etc.) tyrosine-derived polycarbonate poly (DTE-co-DT carbonate), in which the pendant group via the tyrosine—an amino acid—is either an ethyl ester (DTE) or free carboxylate (DT) or combinations thereof. Some embodiments may include the use of all resorbable materials, all non-resorbable materials or a combination of some resorbable materials and some non-resorbable materials. The term "resorbable" encompasses materials considered "bioresorbable", "absorbable" and "bioabsorbable."

In some embodiments, the screw may contain an inorganic material, such as an inorganic ceramic and/or bone substitute material. Exemplary inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

Sterilization

The implantable screws may be sterilizable. In various embodiments, one or more screws may be sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the device, including, but not limited to, gas sterilization, such as, for example, with ethylene oxide or steam sterilization.

Kits

In various embodiments, an implantable device may be packaged in a kit in order to maintain the device in a sterile environment before it is implanted. In various embodiments, a kit is provided comprising one or more implantable screws. The kit may include additional parts combined together with the implantable screw to be used to implant the screw. The kit may include the implantable screw(s) in a first compartment. The second compartment may include instruments needed for implanting the screw (such as for example, implantation tool, driver, etc.). A third compartment may include gloves, drapes, wound dressings and other procedural supplies for maintaining sterility of the implanting process, as well as an instruction booklet. A fourth compartment may include additional needles and/or sutures. In a fifth compartment, the kit may include osteoinductive and/or osteoconductive agents (e.g., BMP) for application into the space created by the contoured head. Each tool may be separately packaged in a plastic pouch that is radiation sterilized. A cover of the kit may include illustrations of the implanting procedure and a clear plastic cover may be placed over the compartments to maintain sterility.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed:

1. A temporary implantable screw for preserving the integrity of an oral socket, the screw comprising:
   a healing abutment head wherein the head ranges in height from about 3 mm to about 5 mm and ranges in diameter at a base of the head from about 3 mm to about 6 mm, wherein the head has a straight wall design defined by a top surface, a bottom base, and side surfaces, wherein the head has smooth rounded edges between the top surface and the side surfaces and between the bottom base and the side surfaces;
   an unthreaded neck extending from the bottom base; and
   a shaft for anchoring the screw in the bone, the shaft including a threaded proximal end extending from the neck and a threaded distal end opposite the proximal end, the shaft comprising a middle portion between the proximal end and the distal end, the shaft having a thread extending continuously across the shaft from the proximal end, through the middle portion to the distal end, the thread being adapted to penetrate bone tissue;

wherein the screw is monolithic and has an arcuate shape between the bottom base of the head and the proximal end of the shaft, a major diameter of the thread is about 2.0 mm or less and a minor diameter of the thread is about 1.8 mm or less, and the minor diameter is less than the major diameter.

2. A temporary implantable screw of claim 1, wherein the screw comprises titanium.

3. A temporary implantable screw of claim 1, wherein the height of the head is 5 mm.

4. A temporary implantable screw of claim 1, wherein a length of the shaft ranges from about 8 mm to about 17 mm, and wherein a threading pitch of the distal end of the shaft allows the screw to stabilize in bone after engagement of about 3 mm to about 4 mm of bone.

5. A temporary implantable screw of claim 1, wherein the screw is coated with a material for growing bone.

6. A temporary implantable screw of claim 1, wherein the screw supports a bone graft material.

7. A temporary implantable screw of claim 1, wherein the distal end comprises a tip adapted for self-drilling.

8. A temporary implantable screw of claim 1, wherein an exterior surface of the head is polished so as to provide a finished surface that smooth and grainless such that the finished surface is resistant to plaque and tartar build up.

9. A temporary implantable screw of claim 1, wherein the screw consists of one material.

10. A temporary implantable screw of claim 1, wherein the height of the head is 3 mm.

11. A temporary implantable screw of claim 1, wherein the height of the head is 4 mm.

12. A temporary implantable screw for preserving the integrity of an oral socket, the screw comprising:
a healing abutment head wherein the head ranges in height from about 3 mm to about 5 mm and ranges in diameter at a base of the head from about 3 mm to about 6 mm, wherein the head has a flared design defined by a top surface, a bottom base, and side surfaces, wherein the head has smooth rounded edges between the top surface and the side surfaces and between the bottom base and the side surfaces;
an unthreaded neck extending from the bottom base; and
a shaft for anchoring the screw in the bone, the shaft including a threaded proximal end extending from the bottom base and a threaded distal end opposite the proximal end, the shaft comprising a middle portion between the proximal end and the distal end, the shaft having a thread extending continuously across the shaft from the proximal end, through the middle portion to the distal end, the thread being adapted to penetrate bone tissue;
wherein the screw is monolithic and has an arcuate shape between the bottom base of the head and the proximal end of the shaft, a major diameter of the thread is about 2.0 mm or less and a minor diameter of the thread is about 1.8 mm or less, and the minor diameter is less than the major diameter.

13. A temporary implantable screw of claim 12, wherein the screw comprises titanium.

14. A temporary implantable screw of claim 12, wherein the diameter of the head increases by 1, 1.5, or 2 mm at the top surface of the head relative to the bottom base.

15. A temporary implantable screw of claim 12, wherein a length of the shaft ranges from about 8 mm to about 17 mm, and wherein a threading pitch of the distal end of the shaft allows the screw to stabilize in bone after engagement of about 3 mm to about 4 mm of bone.

16. A temporary implantable screw of claim 12, wherein the screw is coated with a material for growing bone.

17. A temporary implantable screw of claim 12, wherein the distal end comprises a tip adapted for self-drilling.

18. A temporary implantable screw of claim 12, wherein an exterior surface of the head is polished so as to provide a finished surface that smooth and grainless such that the finished surface is resistant to plaque and tartar build up.

19. A method of preserving an oral socket comprising:
implanting a temporary implantable device into an oral socket in a jawbone of a patient, wherein the implantable device comprises:
at least one implantable screw, the screw comprising:
a healing abutment head wherein the head ranges in height from about 3 mm to about 5 mm and ranges in diameter at a base of the head from about 3 mm to about 6 mm and said head is defined by a top surface, a bottom base, and side surfaces, wherein the head has smooth rounded edges between the top surface and the side surfaces and between the bottom base and the side surfaces,
an unthreaded neck extending from the bottom base, and
a shaft adapted for anchoring the screw in the jawbone, the shaft including a threaded proximal end extending from the neck and a threaded distal end opposite the proximal end, the shaft comprising a middle portion between the proximal end and the distal end, the shaft having a thread extending continuously across the shaft from the proximal end, through the middle portion to the distal end, the thread being adapted to penetrate bone tissue,
wherein the screw is monolithic and has an arcuate shape between the bottom base of the head and the proximal end of the shaft, a major diameter of thread is about 2.0 mm or less and a length of the shaft is about 8 mm to about 17 mm;
incorporating a bone growth material on or near the screw; and
removing the implantable device prior to placement of a dental implant.

* * * * *